United States Patent [19]

Lemmen

[11] Patent Number: 4,774,966
[45] Date of Patent: Oct. 4, 1988

[54] CARPAL TUNNEL SYNDROME SCREENING DEVICE

[76] Inventor: Roger D. Lemmen, 1241 Heather Dr., Holland, Mich. 49423

[21] Appl. No.: 930,320

[22] Filed: Nov. 12, 1986

[51] Int. Cl.⁴ .................................................. A61B 5/10
[52] U.S. Cl. ........................................ 128/774; 73/379
[58] Field of Search ............................... 128/774, 782; 73/379–381; 33/511–512, 515; 272/67–68, 125, 135–136

[56] References Cited

U.S. PATENT DOCUMENTS

| | | | |
|---|---|---|---|
| 3,670,573 | 6/1972 | Kroemer | 73/379 |
| 3,672,219 | 7/1972 | Van Patten | 73/379 |
| 3,752,473 | 8/1973 | La Lanne | 73/381 X |
| 3,848,468 | 11/1974 | Richards | 73/380 |
| 4,173,074 | 11/1979 | Newman et al. | 33/512 X |

FOREIGN PATENT DOCUMENTS

| | | | |
|---|---|---|---|
| 0140871 | 5/1985 | European Pat. Off. | 128/774 |
| 0149029 | 11/1980 | Japan | 73/379 |

OTHER PUBLICATIONS

Dickson et al.; "A Device for Measuring the Force of the Digits of the Hand"; *Bio-Med. Eng.*; GB, vol. 7, No. 6, 7-1972, pp. 270-273.

Primary Examiner—Kyle L. Howell
Assistant Examiner—Angela D. Sykes
Attorney, Agent, or Firm—Price, Heneveld, Cooper, DeWitt & Litton

[57] ABSTRACT

A carpal tunnel syndrome screening device for measuring the strength of or combined force vector generated by the intrinsic hand muscles innervated by the median nerve after is passes through the carpal tunnel includes a base defining a palm support or rest surface and a thumb guide surface. The surfaces are configured to position the thumb of the user for movement in a substantially vertical plane with the thumb positioned at an angle of approximately 45° with respect to the index finger. The device further includes a thumb receiving cradle and a cradle support structure. A force transducer operatively connected to the cradle measures the force created by movement of the thumb. The device provides an objective indication of the presence of carpal tunnel syndrome.

21 Claims, 2 Drawing Sheets

4,774,966

CARPAL TUNNEL SYNDROME SCREENING DEVICE

BACKGROUND OF THE INVENTION

The present invention relates to a device for measuring muscular strength and more particularly to the measurement of the strength of the intrinsic hand muscles innervated by the median nerve after it passes through the carpal tunnel in order to provide an objective indication of the presence of carpal tunnel syndrome.

Generally, the median nerve supplies sensation to the thumb, index finger, middle finger and half of the ring finger. The nerve passes through the wrist beneath the flexor retinaculum or transverse carpal ligament. The transverse carpal ligament and tendons of the flexor muscles define a tunnel through which the median nerve passes. The median nerve innervates three thenar and two lumbrical muscles. Other short muscles of the hand are innervated by the ulnar nerve. The muscles innervated by the median nerve include the abductor pollicis brevis, the opponens pollicis and the superficial head of the flexor pollicis brevis.

Should the median nerve become swollen as it passes through the carpal tunnel or should the carpal ligament become abnormally thickened, pinching or compression of the median nerve results. Swelling of the nerve or surrounding tissues may result from certain diseases, such as diabetes mellitus or rheumatoid arthritis. Unusual strain on the wrist such as that caused by repetitive and strenuous use of the hand may also result in such swelling. When such occurs, the resulting symptoms are referred to as carpal tunnel syndrome. The symptoms include pain, loss of sensation and weakness in the hand.

Generally, diagnosis of carpal tunnel syndrome will not occur until long after onset of the symptoms. Presently, there is no objective way to measure weakness in the hand which might be related to carpal tunnel syndrome and which would provide an early identification of the problem. The earlier diagnosis is accomplished, the more effective treatment procedures will be. If detected early, carpal tunnel syndrome may be treated and relief obtained short of surgical procedures. Surgical procedures are not always effective. Carpal tunnel syndrome is a significant factor in the work place resulting in lost work time and compensation claims. Early identification and treatment may reduce the cost associated with th disease.

A need exists for a device and method which can detect weakness in the hand which may be related to carpal tunnel syndrome and which will provide objective parameters which indicate the need for further evaluation.

SUMMARY OF THE INVENTION

In accordance with the present invention, the aforementioned needs are fulfilled. Essentially, a device is provided which measures the combined force vector or strength of the intrinsic hand muscles innervated by the median nerve after it passes through the carpal tunnel. The device includes a base defining a palm rest or support surface and a thumb guide surface. The surfaces are configured to position the hand so that movement of the thumb is restricted to substantially a vertical plane with the thumb positioned at an approximately 45° angle with respect to the index finger. A force measuring means receives the thumb at the interphalangeal joint. Restraining and positioning the thumb in such a fashion permits measurement of the strength of or force generated by the intrinsic hand muscles supplied by the median nerve and lessens or omits input from other muscles, including the flexor pollicis longus which flexes the distal phalanx of the thumb but is not innervated by the median nerve after going through the carpal tunnel.

The present invention allows the generation of criteria indicating normal strength. An individual may be tested or screened and the strength indication compared with the predetermined normal strength measurements. Should the individual test indicate weakness, further evaluation would be indicated. An abnormality involving hand strength is likely to worsen if activities are unrestricted. Highly repetitive and strenuous use of the hands may be limited to prevent further degradation. Abnormal weakness or strength may be caused by other factors besides carpal tunnel syndrome. Such include, for example, peripheral neuropathy, cerebral damage, cervical cord damage and neuromuscular disease. The screening procedure permits the physician to evaluate and diagnose cause of the abnormality. The device in accordance with the present invention permits effective screening techniques to be developed, a reduction in lost work time and workers compensation claims and an improvement in the effectiveness of treatment through early identification of the problem.

DETAILED DESCRIPTION OF THE PREFERRED EMBODIMENT

Figure 1:
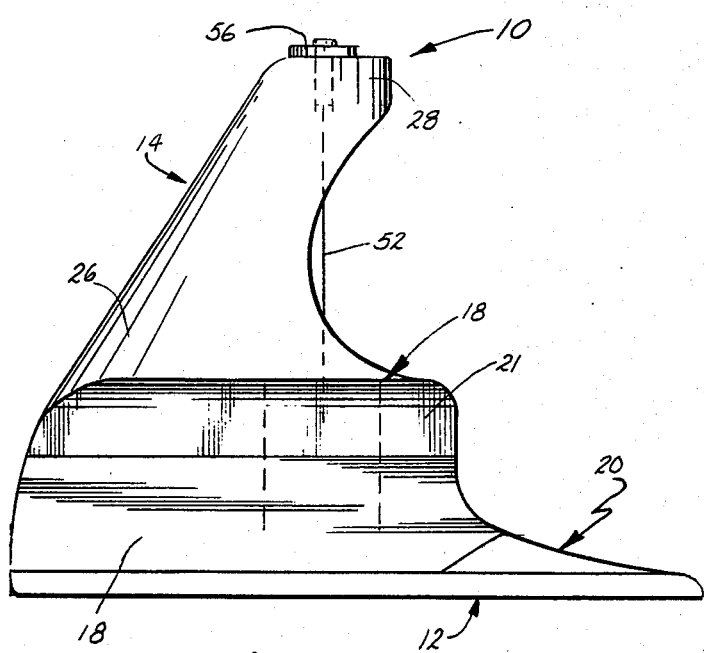
FIG. 1 is a side, elevational view of a carpal tunnel screening device in accordance with the present invention.
Figure 2:
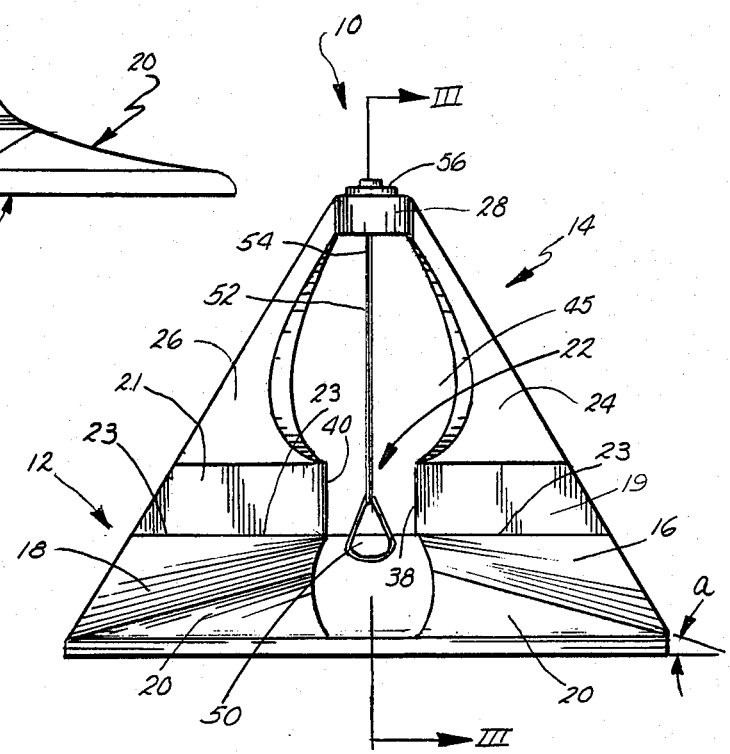
FIG. 2 is a front, elevational view of the device.
Figure 3:
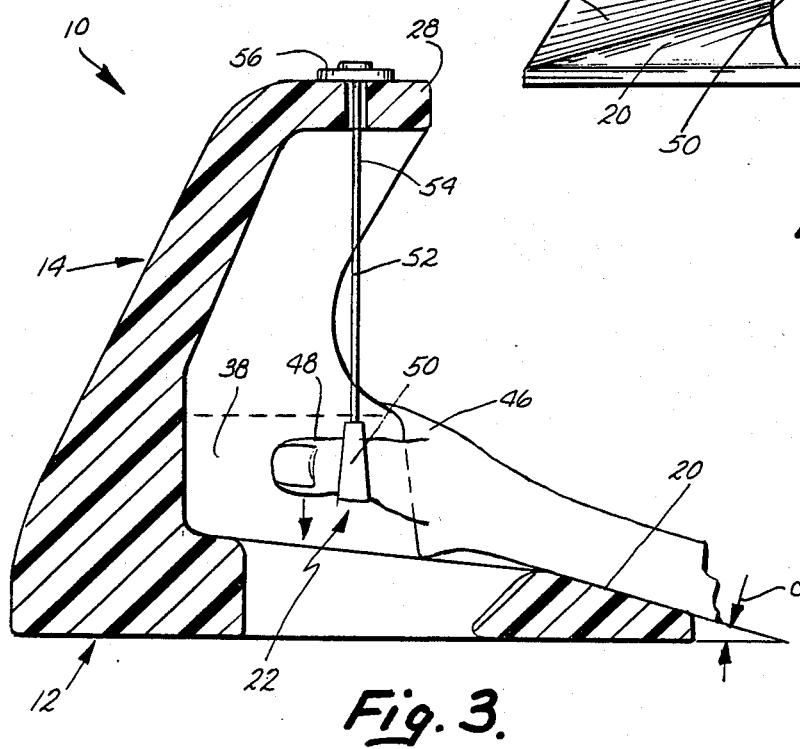
FIG. 3 is a cross-sectional view taken generally along line III—III of FIG. 2.
Figure 4:
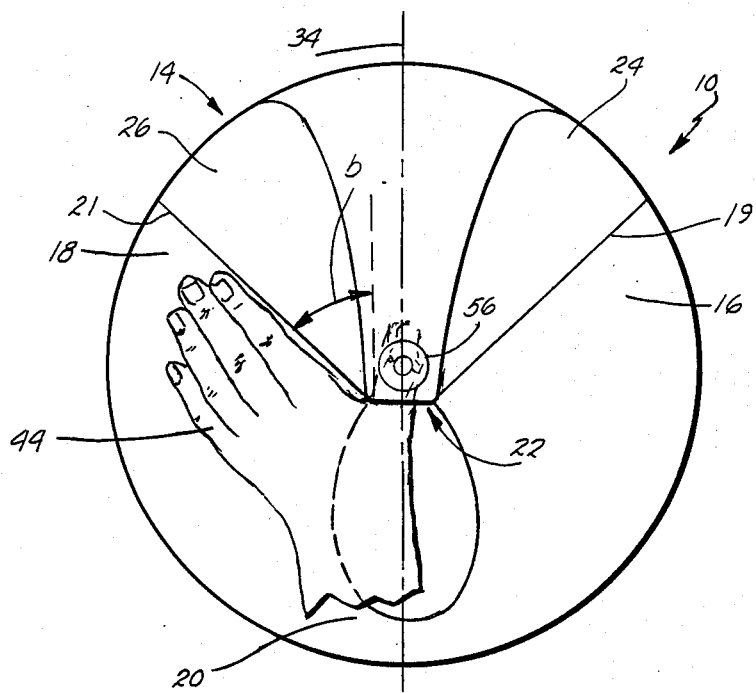
FIG. 4 is a top, plan view of the device.

A preferred embodiment of the carpal tunnel syndrome screening device in accordance with the present invention is illustrated in FIGS. 1-4 and generally designated by the numeral 10. Device 10 includes a base 12 and a tower or support structure 14 joined to the base. Base 12 defines a right hand palm support or rest surface 16, a left hand palm support or rest surface 18, a wrist support surface 20 and a longitudinally extending, centrally positioned thumb slot 22. Opposed sides 24, 26 of base 12 extend upwardly and are joined at a truncated apex 28 positioned directly above thumb slot 22 to form tower 14. Both palm support surfaces 16, 18 are configured so that they assume an angle "a" (FIG. 2) with horizontal of approximately 35°. Surfaces 16, 18, as shown in FIG. 4, join vertical surfaces 19, 21 which assume an angle "b" of approximately 45° with a longitudinal centerline 34 of the device. Surfaces 16, 18 slope downwardly from a lower edge 23 of each surface 19, 21. The wrist support surface 20, as shown in FIG. 3, assumes an angle "c" of approximately 35° with respect to horizontal.

Sidewalls 24, 26 define opposed, spaced, parallel thumb guide surfaces 38, 40. The spacing between surfaces 38, 40 is selected to accommodate the thumb.

Surfaces 16, 18, 19, 20, 21, 38 and 40 are configured so that the patient's thumb 48 is fixed and constrained to move in a substantially vertical plane coincident with longitudinal centerline 34. The slot is dimensioned to limit side to side movement of the thumb.

As shown in FIGS. 3 and 4, the device accommodates both the left and right hands 44, 46 of the individual to be tested. When the hand is positioned on the device with the wrist on surface 20 and the palm on one of the surfaces 16, 18, the hand is angled downwardly and outwardly with respect to the thumb slot. Thumb 48 is positioned between the respective guide surfaces 38, 40 and parallel to a vertical plane extending through centerline 34. The sidewall portions defining surfaces 19, 21 and the guide surfaces 38, 40 define wedges which properly position the thumb at a 45° angle with respect to the adjacent index finger, as shown in FIG. 4. The hand is positioned and fixed so that the direction of thumb movement is limited. Movement is permitted substantially only in a direction caused by the intrinsic hand muscles innervated by the median nerve after it passes through the carpal tunnel.

In order to measure the strength of the muscles or the force vector generated by these muscles in such movement of the thumb, a force measuring means is provided. In the presently preferred form, the force measuring means includes a generally semicircular or half moon thumb cradle 50. Cradle 50 is suspended by a force transmission member, rod, line or chain 52. An upper end 54 of member 52 is connected to a force transducer or dynamometer 56. Dynamometer 56 measures the force generated by the downward movement of the thumb, as illustrated in FIG. 3. Transducer 56 is preferably a commercially available electric, miniature force transducer. It is connected to an amplifier or other electronic instruments (not shown) for the measurement of forces. Such measurements are performed without significant downward movement or motion of the thumb with respect to the transducer. One type of acceptable miniature force transducer is manufactured for measurement of tensile forces. The force applied to cradle 50 is transmitted to the transducer 56 by member 52. In one available transducer, the force is applied to a measuring body whose deformation is converted by four full-bridge strain gauges into a force proportional electrical signal. This electrical signal or output from the transducer may be amplified by readily available components to provide a readout. Other force transducers may be used. Any device which is capable of measuring the forces involved and providing a readout proportional thereto may be used.

Use and Operation

Figure 5:
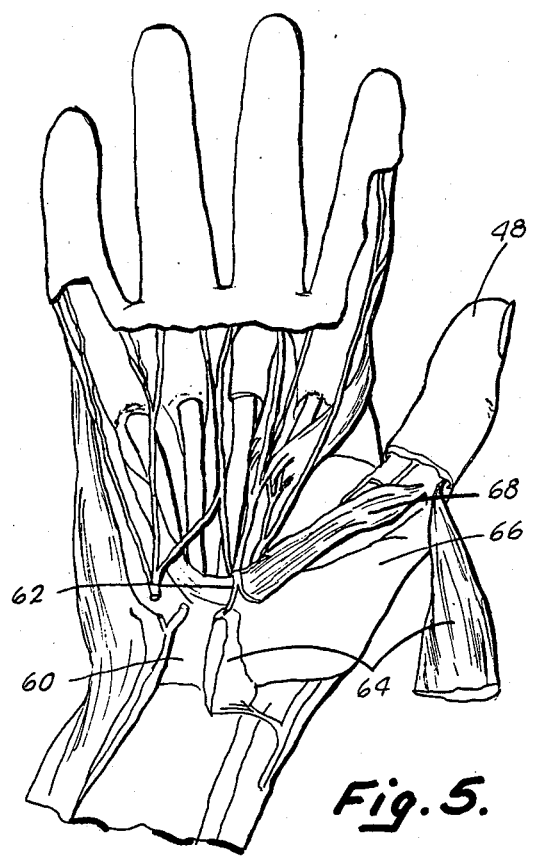
FIG. 5 is a palmar view of a partially dissected hand showing the median nerve and the principal muscles innervated thereby.

FIG. 5 illustrates a partially dissected human hand. As shown, the transverse carpal ligament 60 extends over the carpal bones of the wrist. A median nerve 62 extends beneath ligament 60. Nerve 62 innervates the abductor pollicis brevis muscle 64 (shown cut in FIG. 5), the opponens pollicis muscle 66 and the superficial head of the flexor pollicis brevis muscle 68. In order to isolate the force measured by the device, the thumb and hand are positioned on device 10 so that cradle 50 is at the interphalangeal joint. Sidewalls 24, 26 and their respective surfaces 19, 21 define a wedge which is inserted into the space between the thumb and the index finger. The hand is positioned and fixed. The force measured upon downward movement of the thumb is that generated by such intrinsic hand muscles supplied by the median nerve.

By testing a statistically significant number of individuals from appropriate control groups, measurements of the strength of these muscles may be made to determine a "normal" strength value. Once a value or range of values which indicate "normal" strength is determined, the device may be used to screen or test individuals and compare their results against such normal values.

In a typical screening procedure, multiple readings would be taken to determine an average strength value for the individual. If the strength is that indicated for the normal individual, no objective weakness would be indicated. This would provide the physician with an objective indication that there is no carpal tunnel syndrome associated weakness with the individual. The objective indication of normal strength would not, however, exclude the presence of mild disease.

If the user tests at an abnormally low strength level, further evaluation would be advisable. Such low levels would indicate that highly repetitive, strenuous use of the hands be eliminated. Various tests could then be conducted on the individual to identify the precise nature of the disease and eliminate other causes besides those associated with carpal tunnel syndrome. The present invention provides, for the first time, an objective indication or screening capability. An early identification of a potential problem may be made and the effectiveness of treatment increased. Restriction of the individual's activities may prevent worsening of the problem and avoid the need for surgical treatment. In the work environment, the individual could be moved to a different job in which strain on the wrist would be minimized. This would limit the costs involved with lost work time and the like before a severe problem occurs.

In view of the foregoing description, those of ordinary skill in the art may envision various modifications which would not depart from the inventive concepts disclosed herein. For example, shims may be provided to reduce the spacing between thumb guide surfaces 38, 40 to adapt the device to a smaller than average hand. The principal consideration is to limit movement of the thumb to a defined plane along a defined vector. Some limited nonvertical movement should not affect the validity of the output since the distances involved are extremely small. Further, it is believed that other force measuring means besides the dynamometer, cradle and flexible transmission means disclosed could be employed. This approach is, however, presently preferred. It is, therefore, expressly intended that the above description should be considered as only that of the preferred embodiment. The true spirit and scope of the present invention may be determined by reference to the appended claims.

The embodiments of the invention in which an exclusive property or privilege is claimed are defined as follows:

1. A carpal tunnel syndrome screening device for measuring the combined force vector from intrinsic hand muscles innervated by the median nerve after it passes through the carpal tunnel, said device comprising:

a base defining a palm rest surface and a thumb guide surface, said surfaces configured to position a thumb of a user for movement in substantially a single plane so that movement of the thumb is permitted substantially only in a direction caused by the intrinsic hand muscles innervated by the median nerve after it passes through the carpal tunnel;

a thumb receiving cradle;

cradle support means for supporting said thumb receiving cradle adjacent said thumb guide surface with the cradle positioned to receive the thumb at the interphalangeal joint, said cradle support means being joined to said base; and force measuring means operatively connected to said cradle for measuring a downward force exerted on the cradle by the thumb of the user.

2. A carpal tunnel syndrome screening device as defined by claim 1 wherein said palm rest surface defines an angle "a" of approximately 35° with respect to horizontal and said base further defines a wrist support surface.

3. A carpal tunnel syndrome screening device as defined by claim 2 wherein said palm rest surface and said thumb guide surface are configured so that the thumb of a user assumes an angle "b" of approximately 45° with respect to an adjacent index finger when the thumb is adjacent the thumb guide surface and the user's palm is on the palm rest surface.

4. A carpal tunnel syndrome screening device as defined by claim 1 wherein said base defines another palm rest surface and another thumb guide surface, said thumb guide surfaces extending in spaced, parallel relationship with respect to each other to define a thumb receiving slot.

5. A carpal tunnel syndrome screening device as defined by claim 4 wherein said base is substantially symmetrical with respect to a longitudinal centerline.

6. A carpal tunnel syndrome screening device as defined by claim 5 wherein said palm rest surfaces each define an angle "a" of approximately 35° with respect to horizontal.

7. A carpal tunnel syndrome screening device as defined by claim 6 wherein said palm rest surfaces and said thumb guide surfaces are configured so that the thumb of a user assumes an angle "b" of approximately 45° with respect to an adjacent index finger when the thumb is adjacent one of the thumb guide surfaces and the user's palm is on one of the palm rest surfaces.

8. A carpal tunnel syndrome screening device as defined by claim 7 wherein said cradle support means comprises:

a tower joined to said base and having a portion extending over and above said thumb guide surfaces; and a force transmission means extending from said tower to said cradle, said force transmission means being connected to said force measuring means.

9. A carpal tunnel syndrome screening device as defined by claim 10 wherein said force measuring means is a dynamometer.

10. A carpal tunnel syndrome screening device as defined by claim 1 wherein said cradle support means comprises:

a tower joined to said base and having a portion extending over and above said thumb guide surface; and a force transmission means extending from said tower to said cradle, said force transmission means being connected to said force measuring means.

11. A carpal tunnel syndrome screening device as defined by claim 8 wherein said force measuring means is a dynamometer.

12. An apparatus for measuring the force generated by hand muscles innervated by the median nerve and adapted to support a user's thumb and position the thumb for movement in a defined plane, said apparatus comprising:

a hand support, said support defining a longitudinally extending slot, a right hand palm support surface and a left hand palm support surface, said surfaces being on opposite sides of said slot and configured to position the thumb of either hand in the slot for movement in a vertical plane with the thumb assuming approximately a 45° angle with the adjacent index finger; and force measuring means disposed at least in part within said slot for receiving the thumb at the interphalangeal joint of the thumb and measuring the force generated by the muscles of the hand which move the thumb downwardly within the slot.

13. An apparatus as defined by claim 12 wherein said palm support surfaces assume an angle "a" of approximately 35° with respect to horizontal.

14. An apparatus as defined by claim 13 wherein said force measuring means comprises:

a thumb cradle;

a support on the base;

a dynamometer on said support; and means connected to said dynamometer for suspending said thumb cradle within said slot.

15. An apparatus as defined by claim 14 wherein said slot defines opposed, parallel, spaced thumb guide surfaces.

16. An apparatus as defined by claim 16 wherein said means connected to said dynamometer comprises an elongated member.

17. An apparatus as defined by claim 13 wherein said slot defines opposed, parallel, spaced thumb guide surfaces and said hand support further defines a wrist support surface.

18. A method of testing individuals for hand weakness possibly related to carpal tunnel syndrome, comprising the steps of:

positioning the hand of an individual so that the thumb assumes an angle of approximately 45° with respect to the index finger and the palm is angled with respect to horizontal and the thumb is positioned for movement in substantially a single vertical plane;

fixing the hand in such position;

measuring the force generated by the intrinsic hand muscles innervated by the median nerve upon downward movement of the thumb in said plane; and comparing the force determined by said measuring step with a predetermined normal force.

19. A method as defined by claim 18 wherein said step of measuring the force includes the steps of:

placing the thumb within a cradle;

connecting the cradle to a dynamometer; and recording the output of the dynamometer.

20. A method as defined by claim 19 wherein said step of measuring the force determines the force generated by said intrinsic hand muscles at the interphalangeal joint of the thumb.

21. A method as defined by claim 18 wherein said step of measuring the force determines the force generated by said intrinsic hand muscles at the interphalangeal joint of thumb.

* * * * *

UNITED STATES PATENT AND TRADEMARK OFFICE
CERTIFICATE OF CORRECTION

PATENT NO. : 4,774,966

DATED : October 4, 1988

INVENTOR(S) : Roger D. Lemmen

It is certified that error appears in the above-identified patent and that said Letters Patent is hereby corrected as shown below:

Abstract of the Disclosure, line 4:
    "is" should be --it--;

Column 1, line 49:
    "th" should be --the--;

Column 5, line 55, claim 9:
    "claim 10" should be --claim 8--;

Column 5, line 67, claim 11:
    "claim 8" should be --claim 10--;

Column 6, line 32, claim 16:
    "claim 16" should be --claim 15--; and

Column 6, line 67, claim 21:
    Before "thumb" insert --the--.

Signed and Sealed this

Eighteenth Day of April, 1989

Attest:

DONALD J. QUIGG

*Attesting Officer*    *Commissioner of Patents and Trademarks*